US006790638B1

(12) United States Patent
Carosella et al.

(10) Patent No.: US 6,790,638 B1
(45) Date of Patent: Sep. 14, 2004

(54) METHOD FOR SELECTING TUMOURS EXPRESSING HLA-G, SENSITIVE TO ANTICANCER TREATMENT AND USES

(75) Inventors: Edgardo Delfino Carosella, Paris (FR); Jean Dausset, Paris (FR); Philippe Moreau, Viry-Chatillon (FR); Pascale Paul, Paris (FR); Nathalie Rouas-Freiss, Paris (FR)

(73) Assignee: Commissariat a l'Energie Atomique, Paris (FR)

(*) Notice: Subject to any disclaimer, the term of this patent is extended or adjusted under 35 U.S.C. 154(b) by 0 days.

(21) Appl. No.: 09/622,583

(22) PCT Filed: Feb. 19, 1999

(86) PCT No.: PCT/FR99/00386

§ 371 (c)(1),
(2), (4) Date: Oct. 13, 2000

(87) PCT Pub. No.: WO99/42128

PCT Pub. Date: Apr. 26, 1999

(30) Foreign Application Priority Data

Feb. 20, 1998 (FR) ............................................. 98 02071
Jul. 24, 1998 (FR) ............................................. 98 09470

(51) Int. Cl.⁷ ......................... C12P 21/06; C01N 33/52; C07K 1/00
(52) U.S. Cl. ......................... 435/69.1; 435/7.2; 530/351
(58) Field of Search ............................... 435/69.1, 7.2, 435/6; 530/351

(56) References Cited

U.S. PATENT DOCUMENTS 5,750,339 A * 5/1998 Smith ............................ 435/6

FOREIGN PATENT DOCUMENTS

| EP | 0 586 627 A | 10/1993 |
| EP | 0 677 582 | 10/1995 |
| WO | WO 96 31604 A | 10/1996 |

OTHER PUBLICATIONS

Klein B et al. HLA class I antigen expression in human solid tumors. Israel J.Med.Sci., 32(12): 1238–1243, 1996.*
Benussan et al. Detection of membrane–bound HLA–G translated products with a specific monoclonal antibody. Proc. Natl. Acad. Sci. USA., vol. 92, pp. 10292–10296, 1995.*
Amiot et al., "HLA—G transcription studies during the different stages of normal and malignant hematopoiesis" Tissue Antigens, vol. 48, No. 5, Nov. 1, 1996, pp. 609–614, XP002086255 see the whole document.
Amiot et al., "Distribution of HLA—G alternative mRNAs including soluble forms in normal lymphocytes and in lymphoid cell–derived leukemia" European Journal of Immunogenetics, vol. 23, No. 4, Aug. 1, 1996, pp. 311–320, XP002086256 see the whole document.
P. Paul et al., "HLA—G Expression in Melanoma: A Way For Tumor Cells To Escape From Immunosurveillance" Proceedings of Natural Academy of Sciences, USA, vol. 95, Apr. 1998, pp. 4510–4515, XP002100587 see p. 4510, col. 2, paragraph 1–paragraph 3, see p. 4511, col. 1, paragraph 3, see p. 4514, col. 2, paragraph 4, see p. 4515, col. 1, paragraph 2.
Y. Yang et al., "Expression of HLA–G In Human Mononuclear Phagocytes and Selective Induction By IFN–Gamma" The Journal of Immunology, vol. 156, 1996, pp. 4224–4231, XP002100588 see p. 4224, col. 2, paragraph 2, see p. 4225, col. 2, paragraph 2, see p. 4230, col. 1, paragraph 2–paragraph 3.
Moreau et al., "Transcrit diff rentiels du g ne du CMH" Comptes Rendus Des Seances De L'Academie Des Sciences Serie III: Sciences De La Vie, vol. 318, Jan. 1, 1995, pp. 837–842, XP002086257 cited in the application, see whole document.
Kirszenbaum et al: "An alternatively spliced form of HLA–G Mrna" Proceedings of the National Academy of Sciences of USA, vol. 91, May 1, 1994, pp. 4209–4213, XP002086258 cited in the application.
Perez et al: "The CD94/NKG2–A inhibitory receptor complex is involved in natural killer cell–mediated recognitaion of cells expressing HLA–G1" Journal of Immunology, vol. 158, No. 12, Jun. 15, 1997, pp. 5736–5743, XP002086259.
Rouas et al: "The alpha domain of HLA–G1 and HLA–G2 inhibits cytoxicity induced by natural killer cells: Is HLA—G the public ligand for natural killer cell inhibitory receptors?" Proceedings Of The National Academy Of Sciences Of USA, vol. 94. May 1, 1997, pp. 5249–5254 XP002086260 cited in application.
Rouas et al., "Direct evidence to support the role of HLA—G in protecting the fetus from maternal uterine natural killer cytolysis" Proceedings Of The National Academy Of Sciences Of USA, vol. 94, Oct. 1, 1997, pp. 11520–11525, XP0002086261.

* cited by examiner

Primary Examiner—Jeffrey Fredman
Assistant Examiner—Suryaprabha Chunduru
(74) Attorney, Agent, or Firm—Oblon, Spivak, McClelland, Maier & Neustadt, P.C.

(57) ABSTRACT

The invention concerns a method for selecting tumours expressing HLA-G, sensitive to an anticancer treatment, which inhibits or prevents the HLA-G activity of said tumours and the uses thereof. Said method enable to establish either the HLA-G, transcription profile of a solid tumour or the HLA-G expression profile of a solid tumour. The method for establishing the HLA-G transcription profile consists in: (i) drawing a tumoral sample; (ii) extracting the mRNA; (iii) reverse transcription (RT) of said RNA: (iv) successive or simultaneous amplification of the cDNA's obtained in (iii) in the presence of primers specific to each HLA-G isoform and analysing the resulting amplification products, by electrophoresis and/or specific hybridisation and (v) establishing said sample HLA-G transcription profile. The method for establishing the HLA-G expression profile consists in: (i) drawing a tumoral sample; (ii) optionally marking said sample cells; (iii) carrying out a lysis of the cells; (iv) contacting said cells which have been subjected to lysis with different antibodies directed against the class I HLA-G antigens, to form, optionally HLA-G isform/antibodies complexes; and (v) establishing said sample HLA-G expression profile by detecting the complexes formed in step (iv).

11 Claims, 12 Drawing Sheets

METHOD FOR SELECTING TUMOURS EXPRESSING HLA-G, SENSITIVE TO ANTICANCER TREATMENT AND USES

BACKGROUND OF THE INVENTION

FIELD OF THE INVENTION

The present invention relates to a method for selecting solid tumours which are sensitive to anticancer treatment, which inhibits or prevents the HLA-G activity of said solid tumours, and to uses thereof.

DISCUSSION OF THE BACKGROUND

Major histocompatibility complex (MHC) antigens are divided up into several classes, class I antigens (HLA-A, HLA-B and HLA-C) which exhibit 3 globular domains ($\alpha 1$, $\alpha 2$ and $\alpha 3$) and whose $\alpha 3$ domain is associated with $\beta 2$ microglobulin, class II antigens (HLA-DP, HLA-DQ and HLA-DR) and class III antigens (complement).

Class I antigens comprise, besides the abovementioned antigens, other antigens, so-called unconventional class I antigens, and in particular the HLA-E, HLA-F, and HLA-G antigens; the latter, in particular, is expressed by extravillous trophoblasts of normal human placenta and thymic epithelial cells.

The sequence of the HLA-G gene (HLA-6.0 gene) was described by Geraghty et al. (Proc. Natl. Acad. Sci. USA, 1987, 84, 9145–9149): it comprises 4396 base pairs and exhibits an intron/exon organization which is homologous to that of the HLA-A, -B and -C genes. More specifically, this gene comprises 8 exons, 7 introns and a 3' untranslated end; the 8 exons correspond respectively to: exon 1: signal sequence, exon 2: $\alpha 1$ extracellular domain, exon 3: $\alpha 2$, extracellular domain, exon 4: $\alpha 3$ extracellular domain, exon 5: transmembrane region, exon 6: cytoplasmic domain I, exon 7: cytoplasmic domain II (untranslated), exon 8: cytoplasmic domain III (untranslated) and 3' untranslated region (Geraghty et al., mentioned above: Ellis; et al., J. Immunol., 1990, 144, 731–735; Kirszenbaum M. et al., Oncogeny of hematopoiesis. Aplastic anemia Eds. E. Gluckman, L. Coulombel, Colloque INSERM/John Libbey Eurotext Ltd). However, the HLA-G gene differs from the other class I genes in that the in-frame translation stop codon is located in the second codon of exon 6; consequently, the cytoplasmic region of the protein encoded by this HLA-6.0 gene is considerably shorter than the cytoplasmic regions of the HLA-A, -B and -C proteins.

These HLA-G antigens are essentially expressed by the cytotrophoblastic cells of the placenta and are considered to play a role in protecting the foetus (absence of rejection by the mother). In addition, since the HLA-G antigen is monomorphic, it may also be involved in placental cell growth or function (Kovats et al., Science, 1990 248, 220–223).

Other research relating to this unconventional class I antigen (Ishitani et al., Proc. Natl. Acad. all. Sci. USA, 1992, 89, 3947–3951) has shown that the primary transcript of the HLA-G gene can be spliced in w several ways, and produces at least 3 distinct mature mRNAs: the primary transcript of HLA-G provides a 1200-bp complete copy (G1), a 900-bp fragment (G2) and a 600-bp fragment (G3).

The G1 transcript does not comprise exon 7, and corresponds to the sequence described by Ellis et al. (mentioned above), i.e. it encodes a protein which comprises a leader sequence, three external domains, a transmembrane region and a cytoplasmic sequence. The G2 mRNA does not comprise exon 3, i.e. it encodes a protein in which the $\alpha 1$ and $\alpha 3$ domains are directly joined; the G3 mRNA contains neither exon 3 nor exon 4, i.e. it encodes a protein in which the $\alpha 1$ domain and the transmembrane sequence are directly joined.

The splicing which prevails so as to obtain the HLA-G2 antigen leads to the joining of an adenine (A) (originating from the domain encoding $\alpha 1$) with an AC sequence (derived from the domain encoding $\alpha 3$), which leads to the creation of an AAC (asparagine) codon in place of the GAC (aspartic acid) codon encountered at the start of the sequence encoding the $\alpha 3$ domain in HLA-G1.

The splicing generated so as to obtain HLA-G3 does not lead to the formation of a new codon in the splicing zone.

The authors of this article also analysed the various proteins expressed: the 3 mRNAs are translated into protein in the 221-G cell line.

Some of the inventors have shown the existence of other spliced forms of HLA-G mRNA: the HLA-G4 transcript which does not include exon 4; the HLA-G5 transcript which includes intron 4 between exons 4 and 5, thus causing a modification of the reading frame during the translation of this transcript and in particular the appearance of a stop codon after amino acid 21 of intron 4; and the HLA-G6 transcript which possesses intron 4, but has lost exon 3 (Kirszenbaum M. et al., Proc. Natl. Acad. Sci. USA, 1994, 91, 4209–4213; European Application EP 0 677 582; Kirszenbaum M. et al., Human Immunol., 1995, 43, 237–241; Moreau P. et al., Human Immunol., 1995, 43, 231–236); they have also shown that these various transcripts are expressed in several types of foetal and adult human cells, in particular in lymphocytes (Kirszenbaum M. et al., Human Immunol., 1995, mentioned above; Moreau P. et al., Human Immunol. 1995, mentioned above).

Some of the inventors have also shown that NK cells express no HLA-G transcript (Teyssier M. et al., Nat. Immunol., 1995, 14, 262–270; Moreau P. et al., Human Immunol., 1997, 52, 41–46).

At least 6 different HLA-G mRNAs thus exist which potentially encode 6 protein isoforms of HLA-G, of which 4 are membrane-bound (HLA-G1, G2, G3 and G4) and 2 are soluble (G5 and G6).

Although the foetus can be considered to be a semi-allograft, the foetal cells survive and are not rejected by the mother; it has become apparent that the HLA-G molecules expressed at the surface of the trophoblasts protect the foetal cells against lysis by maternal natural killer (NK) cells from the uterine decidua and from peripheral blood (Carosella E. D. et al., C. R. Acad. Sci., 318, 827–830; Carosella E. D. et al., Immunol. Today, 1996, 407–409; Rouas-Freiss N. et al., PNAS, 1997, 94, 5249–5254).

Previous studies have shown that the expression of HLA-G molecules at the surface of transfected target cells makes it possible to protect said target cells against the lytic activity of NK cells from the decidual layer of the maternal endometrium (Chumbley G. et al., Cell Immunol., 1994, 155, 312–322; Deniz G. et al., J. Immunol., 1994, 152, 4255–4261; Rouas-Freiss N. et al., Proc. Natl. Acad. Sci., 1997, 94, 5249–5254). It should be noted that these target cells are obtained by transfection with vectors comprising either HLA-G genomic DNA which potentially generates all the alternative transcripts, or with vectors containing the HLA-G1 and HLA-G2 cDNAs encoding the HLA-G1 and HLA-G2 protein isoforms (European Patent Application No. 0 677 582 and Application PCT/FR98/00333).

NK cells express receptors for class I MHC molecules (killer inhibitory receptors or KIR, or NKIR for NK inhibitory receptors) which are responsible for the inhibition of cytotoxicity when these HLA molecules, acting as ligands, are recognized by these receptors; for example, N. Rouas-Freiss et al., (Proc. Natl. Acad. Sci., 1997, 94, 5249–5254) showed that the expression of HLA-G protected K562 (human erythroleukaemia cell line) target cells transfected with the HLA-G1 and G2 isoforms against lysis. These cells are usually sensitive to NK cells.

These results testify to the fundamental role of the HLA-G molecule as an immunotolerance antigen. These results have been broadened to all of the membrane-bound isoforms. The cDNAs encoding the HLA-G1, G2, G3 and G4 isoforms which are expressed, after transfection, in various cell types, in particular transfected K562 cells and M8 tumour cells, inhibit NK and CTL cytotoxic functions.

Given the important role that the HLA-G molecule may play, the inventors, continuing with their work, more particularly studied tumour cells, and gave themselves in particular the aim of providing tools for selecting solid tumours which are sensitive to a treatment which inhibits the HLA-G antigens present in particular on certain tumours.

SUMMARY OF THE INVENTION

The subject of the present invention is a method for establishing the HLA-G transcription profile of a solid tumour with a view to selecting a treatment which is suited to said tumour and/or with a view to monitoring the evolution of said tumour, characterized in that it comprises:

(i) the removal of a tumour sample;

(ii) the extraction of the mRNA from said sample; a modified Chomczynski and Sacchi method using the RNA reagent NOW (Ozyme, France) can in particular be used;

(iii) the reverse transcription (RT) of said RNA;

(iv) the successive or simultaneous amplifications of the cDNAs obtained in (iii), in the presence of primers specific for each HLA-G isoform, and the analysis of the amplification products obtained by electrophoresis and/or specific hybridization and (v) the establishment of the HLA-G transcription profile of said sample.

Preferably, the reverse transcriptions are primed with oligo-dTs on mRNA which is denatured in advance, for example at 65° C., in the presence of a reverse transcriptase such as M-MLV reverse transcriptase (Gibco-BRL, Life technologies).

Also preferably, the cDNA amplification is carried out by polymerase chain reaction (PCR) using primers specific for the various HLA-G isoforms, in accordance with the following tables:

| Primers | Nucleotide sequences | Hybridization temperatures | Isoforms amplified |
|---|---|---|---|
| G.257 | 5'-GGAAGAGGAGACACGGAACA (SEQ ID NO: 1) | 61 | G1, G2, G3 |
| G3.U | 5'-GGCTGGTCTCTGCACAAAGAGA (SEQ ID NO: 2) | | G4, G5, G6 |
| G.526 | 5'-CCAATGTGGCTGAACAAAGG (SEQ ID NO: 3) | 61 | G1, G4, G5 |
| G3.U | 5'-GGCTGGTCTCTGCACAAAGAGA (SEQ ID NO: 4) | | |
| G.-3-4 | 5'-ACCAGAGCGAGGCCAAGCAG (SEQ ID NO: 5) | 65 | G3 |
| G.3.U | 5'GGCTGGTCTCTGCACAAAGAGA (SEQ ID NO: 6) | | |
| G.-3 | 5'-ACCAGAGCGAGGCCAACCCC (SEQ ID NO: 7) | 65 | G2, G6 |
| G3.U | 5'-GGCTGGTCTCTGCACAAAGAGA (SEQ ID NO: 8) | | |
| G.-3 | 5'-ACCAGAGCGAGGCCAACCCC (SEQ ID NO: 9) | 61 | G6 |
| G.i4b | 5'-AAAGGAGGTGAAGGTGAGGG (SEQ ID NO: 10) | | |
| G.526 | 5'-CCAATGTGGCTGAACAAAGG (SEQ ID NO: 11) | 61 | G5 |
| G.i4b | 5'-AAAGGAGGTGAAGGTGAGGG (SEQ ID NO: 12) | | |

| Probes | Nucleotide sequences | Hybridization temperatures (° C.) | Isoforms |
|---|---|---|---|
| GR | 5'-GGTCTGCAGGTTCATTCTGTC (SEQ ID NO: 13) | 60 | HLA-G1, G2, G3, G4, G5, G6 |
| G.647 F | 5'-CCACCACCCTGTCTTTGACT (SEQ ID NO: 14) | 60 | HLA-G1, G2, G5, G6 |
| G.I4 F | GAGGCATCATGTCTGTTAGG (SEQ ID NO: 15) | 55 | HLA-G5, G6 |
| G.927 F | 5'-ATCATGGGTATCGTTGCTGG (SEQ ID NO: 16) | 55 | HLA-G1, G2, G3, G4, G5 and G6 |

(A): the RT-PCR analysis of the HLA-G isoform mRNAs in melanoma cells. pan-HLA-G primers [primer G.257 (exon 2) and 3G.U (untranslated 3' end)] are used for the PCR amplification of the HLA-G transcripts corresponding to the various known HLA-G isoforms. The cDNA from JEG-3 choriocarcinoma cells and first trimester trophoblasts (TRO), and peripheral blood mononucleated cells (PBMC) were used, these cells being used as control cells for high transcription levels and basal transcription levels of HLA-G, respectively. IgR, M8, DRAN and M74 correspond to the amplification of the cDNA of melanoma cell lines. The specific HLA-G bands are revealed by hybridization with the GR-specific probe, which is located on exon 2. The bands corresponding to the transcripts HLA-G1, G2, G3, G4 and G5 are indicated with arrows. The PCR products which were coamplified during the same reaction using β-actin primers are detected on the same membrane with the aid of a β-actin probe;

(B): this figure corresponds to the RT-PCR detection of alternative transcripts in melanoma cells. Primer 3 is specific for the HLA-G2 and soluble HLA-G2 (G6) isoforms which do not possess exon 3. Primer 3.4 makes it possible to distinguish the HLA-G3 mRNA transcripts. Primers G.526 and 14b amplify specifically the HLA-G5 transcript, which corresponds to the soluble form. The PCR products which were coamplified during the same reaction using β-actin primers are detected on the same membrane with the aid of a β-actin probe;

(C): this figure corresponds to the RT-PCR analysis of the HLA-G mRNA in melanoma cells. pan-HLA-G primers [primer G.257 (exon 2) and 3G.U (untranslated 3' end)] are used for the PCR amplification of the HLA-G transcripts corresponding to the various known HLA-G isoforms. The cDNA from JEG-3 choriocarcinoma cells was used, these cells being used as control cells for high transcription levels. IgR, M8 and DRAN correspond to the amplification of the cDNA melanoma cell lines. The specific HLA-G bands are revealed by hybridization with the GR-specific probe, which is located on exon 2. The bands corresponding to the transcripts HLA-G1, G2, G3, G4 and G5 are indicated with arrows. The PCR products which were coamplified during the same reaction using β-actin primers are detected on the same membrane with the aid of a β-actin probe.

Figure 2:
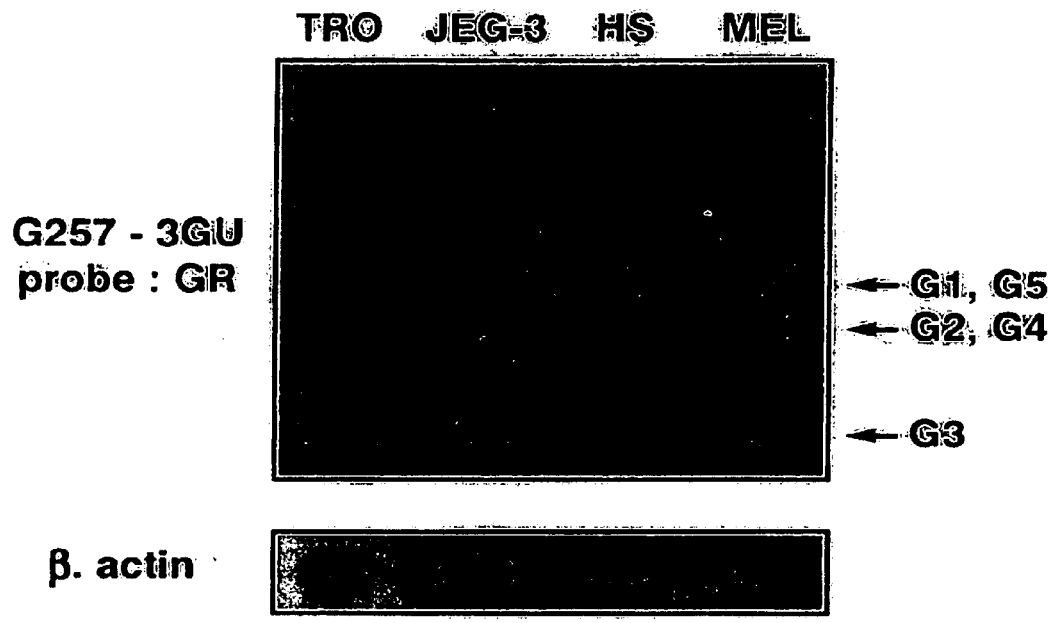

FIG. 2 illustrates the RT-PCR analysis of the HLA-G isoform mRNAs in the biopsies of melanoma metastases (in vivo and ex vivo analysis of skin). The pan-HLA-G primers G.257 and 3G.U are used for the RT-PCR amplification of the HLA-G transcripts from skin metastases ex vivo (MEL) and from biopsies of healthy skin from the same patient (HS); JEG-3 cells and first trimester trophoblasts are used as controls (high level of HLA-G transcription). The HLA-G specific bands are revealed by hybridization with a GR-specific probe which is located in exon 2. The bands corresponding to the transcripts HLA-G1, G2, G3, G4 and G5 are indicated with arrows.

Figure 3:
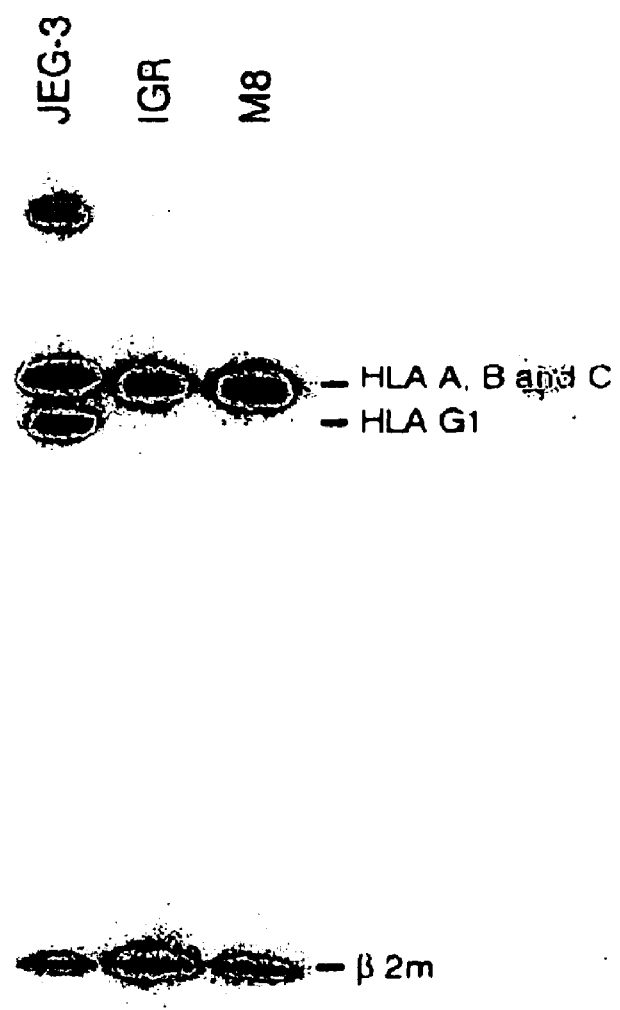

FIG. 3 illustrates the detection of the HLA-G1 proteins in JEG-3 cells but not in IGR and M8 I melanoma cells, with the aid of the monoclonal antibody W6/32: the biotinylated surface proteins of melanoma and JEG-3 cells are immunoprecipitated using the monoclonal antibody W6/32; the immunoprecipitates are separated by SDS-PAGE at 12% and transferred onto cellulose membrane. The class I surface molecules are detected with streptavidin-conjugated peroxidase.

Figure 4:
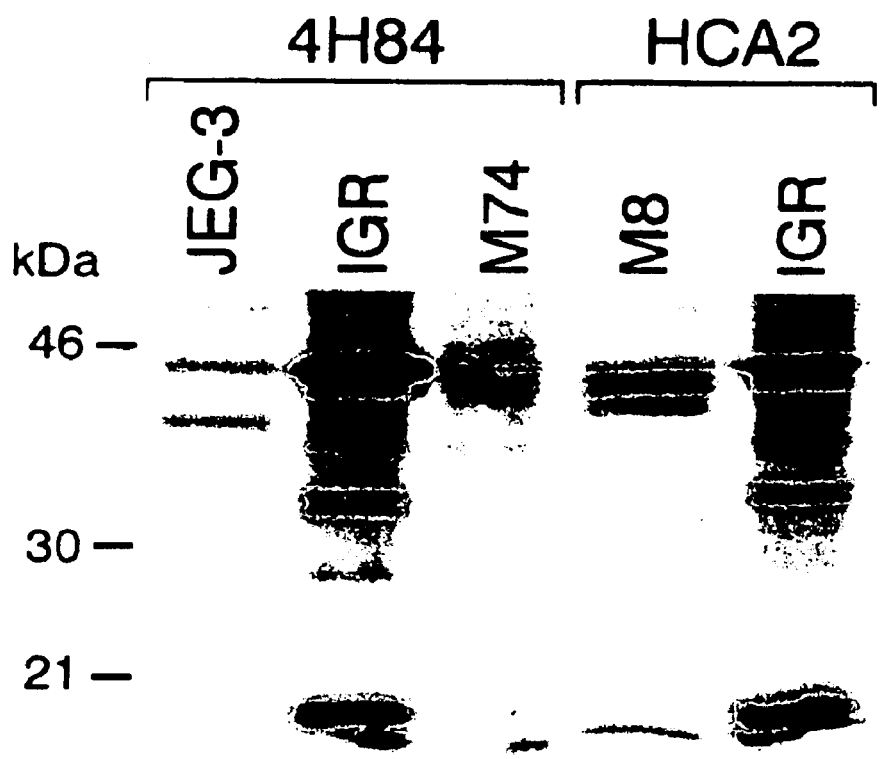

FIG. 4 illustrates the immunoprecipitation of the HLA-G isoforms of IGR melanoma cells with an antibody directed against the heavy chain of free HLA-G and with the monoclonal antibodies 4H84 and HCA2. The cells are labelled for 30 min and immunoprecipitated with the specific antibodies, and the immunoprecipitates are analysed by SDS-PAGE at 10%. The antibody 4H84, which reacts with the HLA-G heavy chain (39-KDa band in JEG-3 cells), exhibits cross-reactions with the HLA-A, -B and/or -C heavy chains (45-KDa band in all the cells tested).

FIG. 5 illustrates:
  (A): the effect of HLA-G expression in the IGR melanoma on sensitivity to lysis by the clone YT2C2-PR. K562 cells which are transfected either with the vector alone, or with the HLA-G1 vector containing the cDNA, or the HLA-G2 vector and the M8, M74, IGR and DRAN lines are used as target cells (T). The clone YT2C2-PR is used as an effector cell (E) in an effector cell/target cell (E/T) ratio of 50/1. The results are expressed as the percentage of lysis recorded in 4 h in a chromium 51-release assay. Spontaneous release never exceeds 10% of the maximum release. This experiment is carried out at least 5 times and, each time, produces the same results;
  (B): the inhibition of the lysis induced by the clone YT2C2-PR is due to an "off" signal which is transmitted by the IGR and DRAN cells. The M8 line is used as a target cell (T) and is chromium labelled. Clone YT2CT-PR is used as an effector cell (E) in an E/T ratio of 50:1. IGR and DRAM cells are added as inhibitor cells in an inhibitor cell/target cell ratio of 100, 50 and 25:1. 0 indicates that no IGR cell was added in the assay;
  (C): the inhibition of the lysis induced by HLA-G-positive melanoma cells (target cells T). This figure illustrates more particularly the effect of HLA-G expression by IGR and DRAN melanoma cells on sensitivity to lysis by the clone YT2C2-PR Several cell lines which are B-EBV, HLA-G negative [HOM (A3, B27, Cw1), BM (A29, B61 Cw2), SPO (A3, B7, Cw7), SWE (A2, B44, Cw5)] are lysed by the clone YT2C2-PR. This clone is used as an effector cell (E) in an E/T ratio of 50/1. The results are expressed as the percentage of lysis recorded in 4 h in a chromium 51-release assay. Spontaneous release never exceeds 10% of the maximum release;
  (D) and (E): these figures show that the M8 HLA-G-negative tumour cells which are transfected with the cDNAs encoding the molecules G1, G2, G3 and G4 inhibit NK lysis (FIG. 5E) and the cytotoxic T responses (FIG. 5D). FIG. 5D comprises, on the x-axis, the effector cells (E) (restricted HLA-A2 lines specific for an influenza peptide)/target cells (T) (transfected M8 lines) ratios and, on the y-axis, the percentage of specific lysis. The table below corresponds to the values obtained in this figure.

| E/T ratio | M8-RSV | G1 | G2 | G3 | G4 | Genomic |
|---|---|---|---|---|---|---|
| 15/1 | 55% | 8% | 39% | 12% | 17% | 30% |
| 7/1 | 52% | 6% | 42% | 10% | 14% | 25% |
| 3/1 | 29% | 2% | 30% | 6% | 12% | 23% |

Figures 5A, 5B:
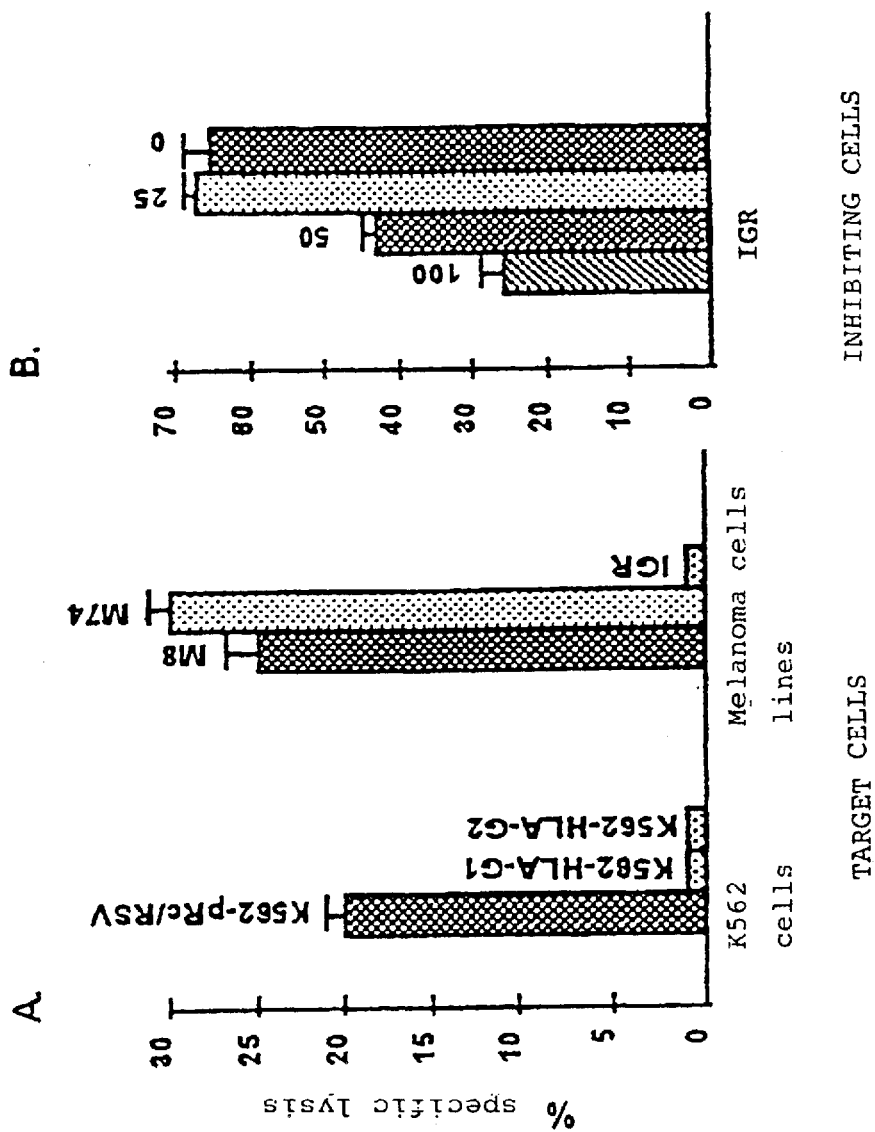
Figure 5C:
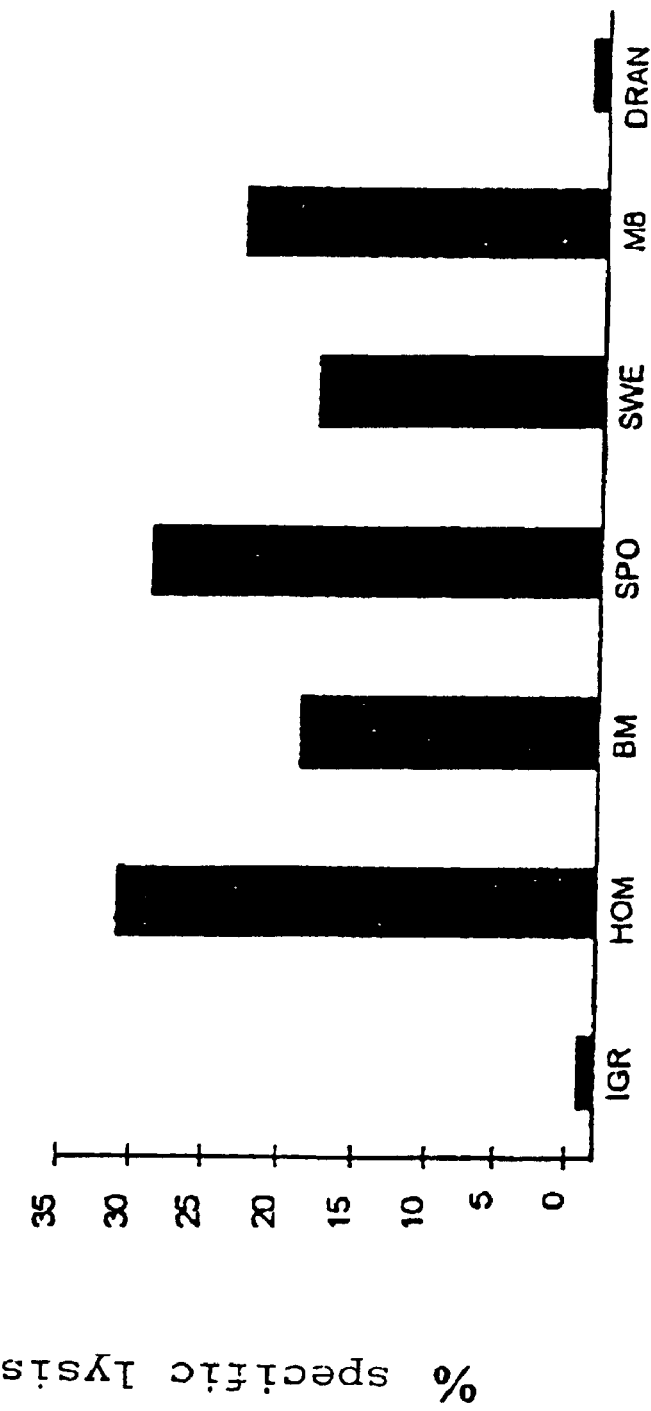
Figure 5D:
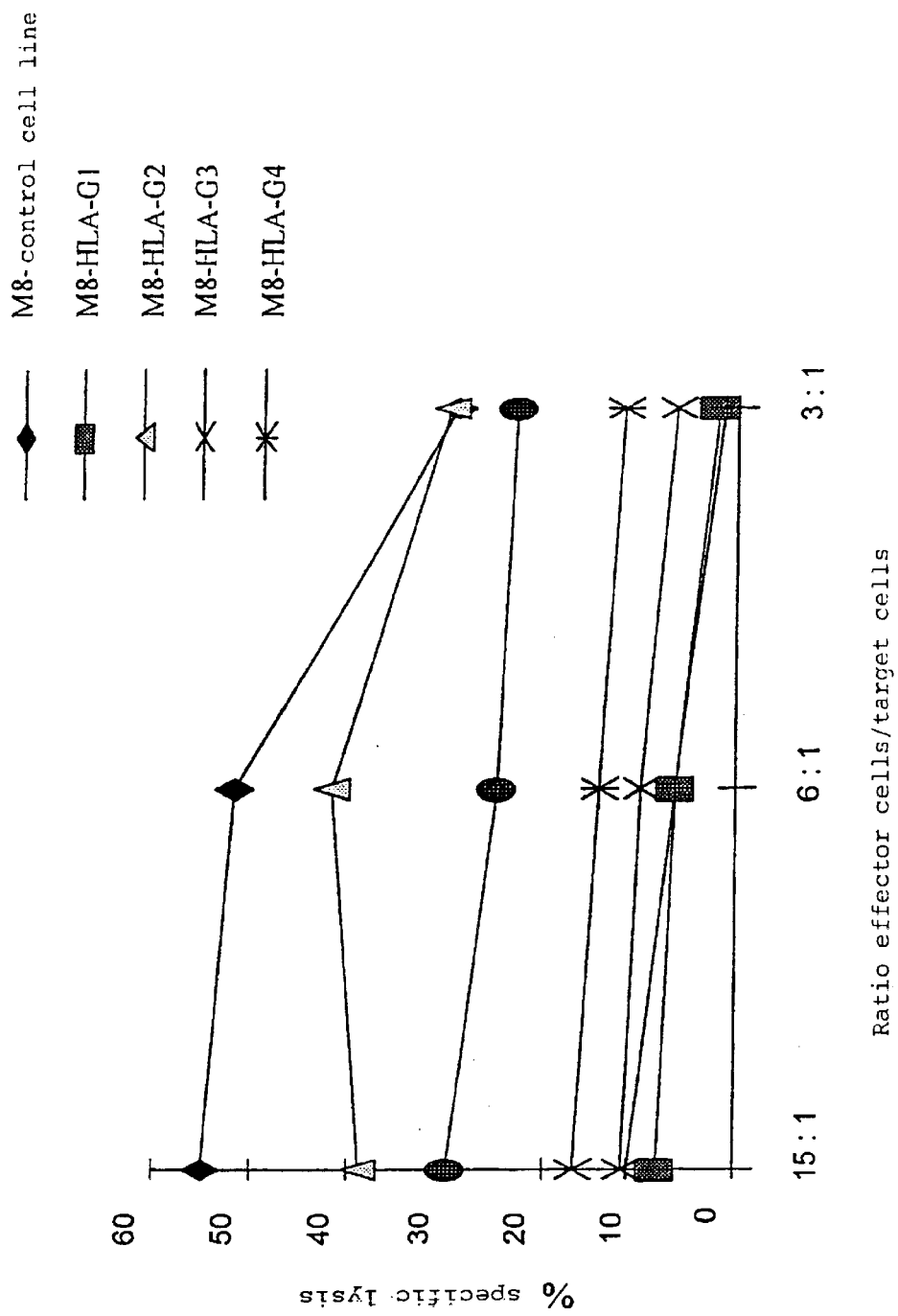
Figure 5E:
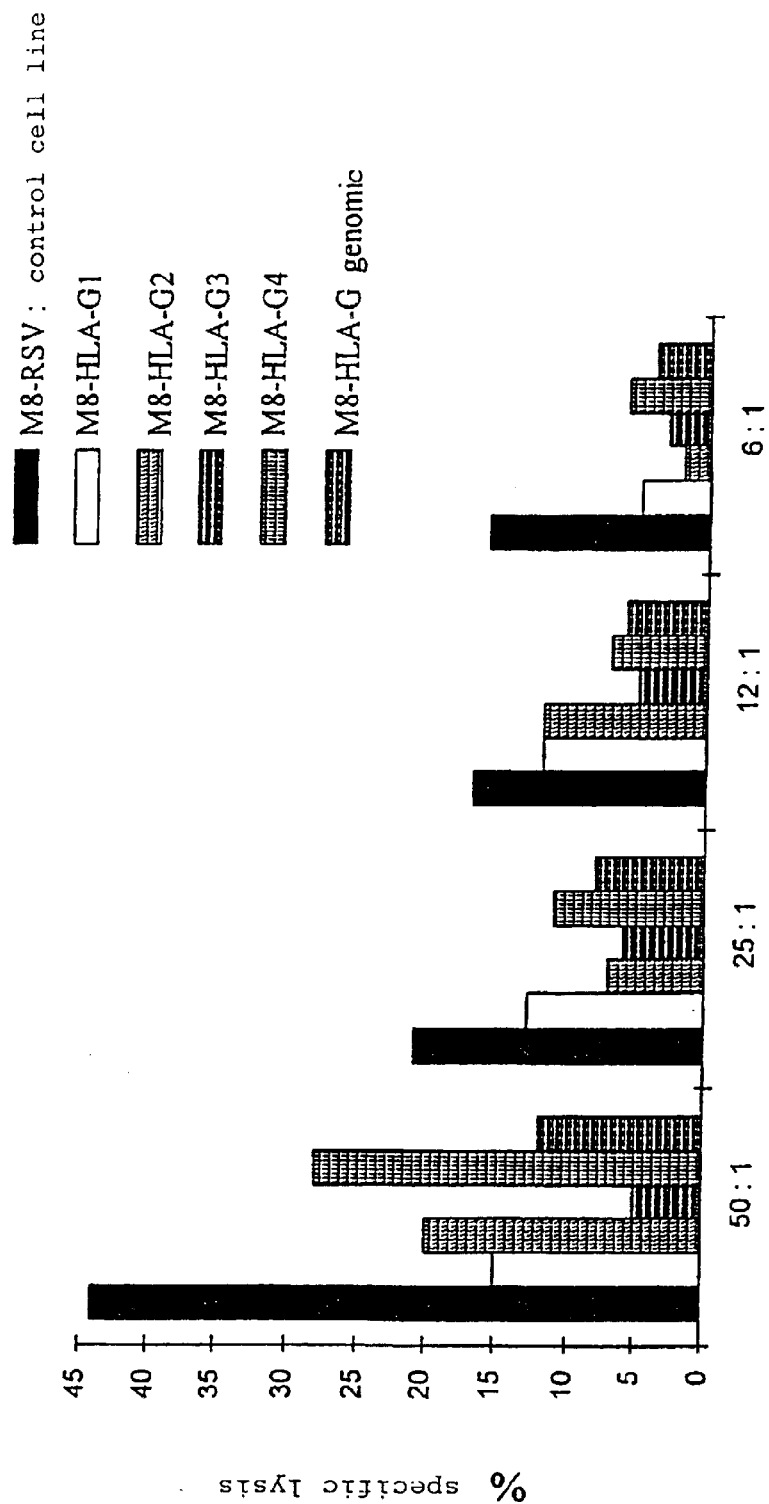

FIG. 5E comprises, on the x-axis, the effector cells (E) (clone YT2C2-PR)/target cells (T) (transfected M8 lines) ratios and, on the y-axis, the percentage of-specific lysis.

Figure 6:
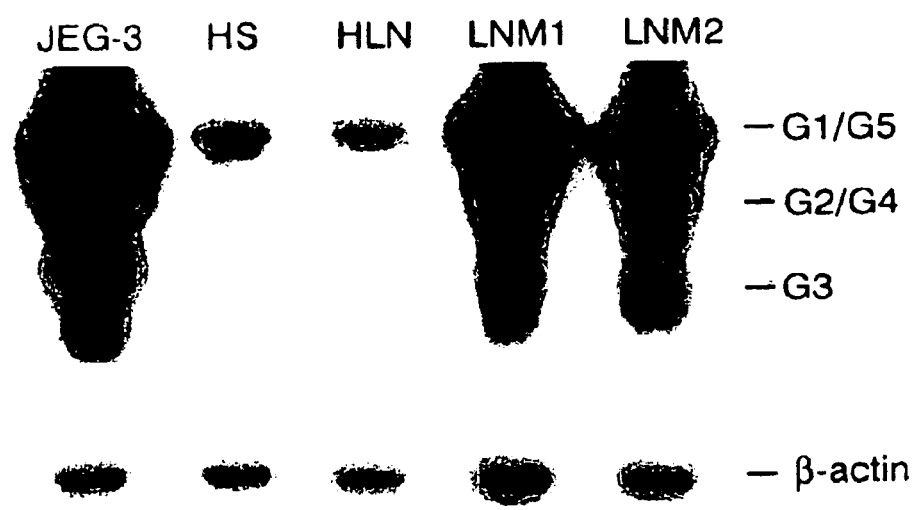

FIG. 6 illustrates the detection of HLA-G transcripts in biopsies of human melanomas. The RT-PCR amplifications are carried out, using the abovementioned primers G.257 and G.3U, on biopsies of healthy skin (HS) and on healthy lymph nodes (HLN), on the one hand, and biopsies of lymph node metastases (LNM1 and LMN2). JEG-3 choriocarcinoma cells are used as control cells for high transcription levels. Specific HLA-G bands are revealed by hybridization with the GR-specific probe which is located on exon 2. The bands corresponding to the transcripts HLA-G1, G2, G3, G4 and G5 are indicated with arrows. The PCR products which were coamplified during the same reaction using the (3-actin primers are detected on the same membrane with the aid of β-actin probe.

Figure 7:
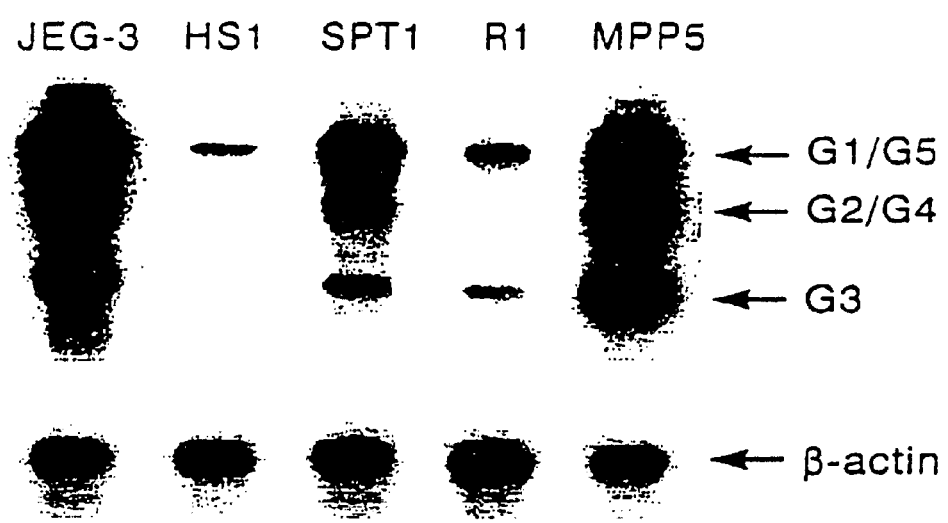

FIG. 7 illustrates the RT-PCR analysis of the HLA-G transcripts in the biopsies of primary melanoma tumours and in the derived MPP5 primary cell cultures (ex vivo analysis). The abovementioned pan-HLA-G primers are used for the amplification from biopsies of healthy skin (HS1), from skin primary tumours (SPT1) and from tumours in regression (R1) which are obtained from the same patient, and from derived primary cells obtained from a skin tumour tissue (MPP5). The MPP5 cells and the SPT1 biopsy exhibit similar HLA-G transcription levels. JEG-3 cells are used as controls for high levels of HLA-G transcription. The HLA-G-specific bands are revealed by hybridization with a GR-specific probe which is located in exon 2. The bands corresponding to the transcripts HLA-G1, G2, G3, G4 and G5 are indicated with arrows. The PCR products which were coamplified during the same reaction using the β-actin primers are detected on the same membrane with the aid of a β-actin-specific-probe.

Figure 8A:
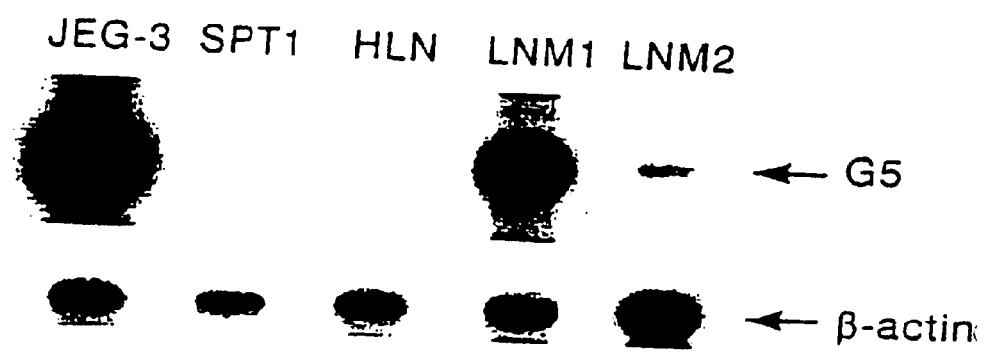
Figure 8B:
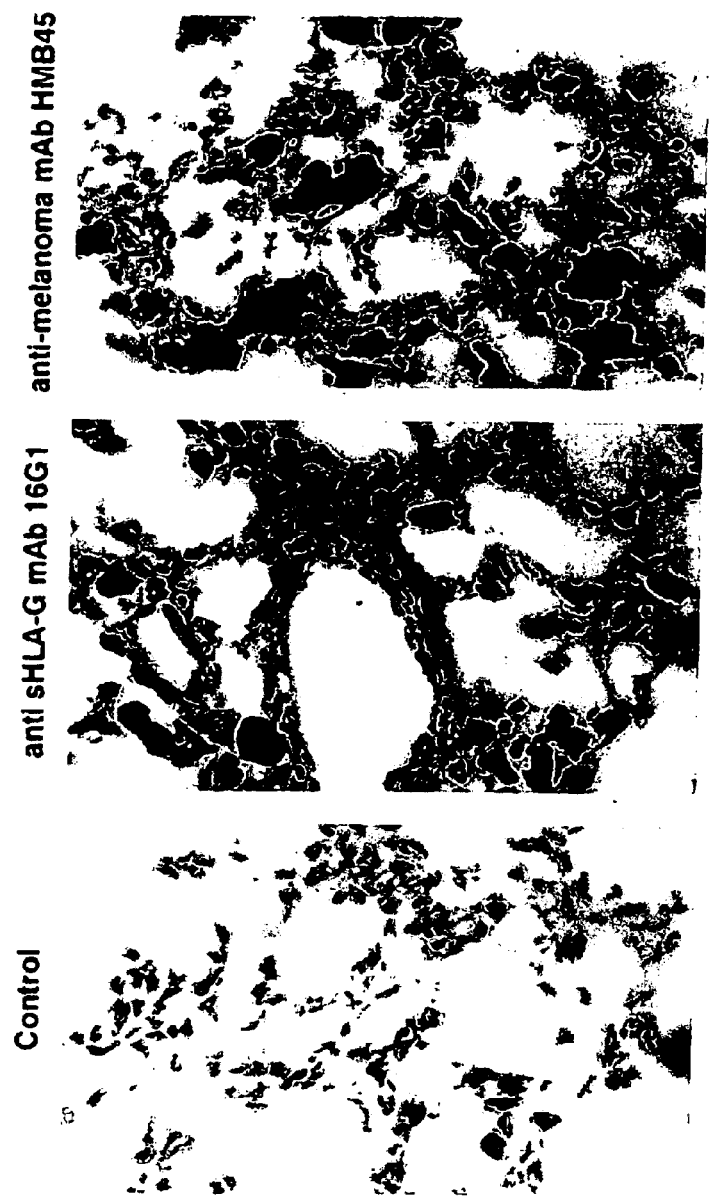

FIG. 8 illustrates:
  (A) the specific detection of HLA-G5 transcripts by RT-PCR in biopsies of melanomas. The amplification of the HLA-G5 transcript from healthy lymph nodes (HLN), from a skin primary tumour (SPT1) and from two biopsies of lymph node metastases (LNM1 and LNM2) is carried out with the aid of the primers G.526 and G.i4b. The band corresponding to the HLA-G5 transcript is detected by hybridization with an I4F probe which is located in intron 4; JEG-3 cells are used as controls (high levels of HLA-G5 transcription). The band corresponding to the HLA-G5 transcript is indicated with arrows. The PCR products which were coamplified in the same reaction using the β-actin primers are- detected on the same membrane with a β-actin-specific probe;

(B) the immunohistochemical analysis of the soluble HLA-G expression in the LNM1 biopsy. Frozen and acetone-fixed sections of the LNM1 biopsy are positively stained with the anti-melanoma antibody HMB45 (DAKO) and the anti-soluble HLA-G antibody 16G1, whereas the negative control gives no staining, using the Envision anti-mouse, peroxidase system (DAKO) and AEC as substrate.

DETAILED DESCRIPTION OF THE INVENTION

The inventors found, surprisingly, that at least some solid tumours express the HLA-G antigen, and showed that this HLA-G antigen plays a functional role in protecting tumour cells (solid tumours) against destruction by NK cells. They also showed the effective presence of certain HLA-G isoforms at the surface of said tumour cells.

However, also surprisingly, depending on the tumour lines, the HLA-G profile (transcripts and proteins) is different.

For example, in some melanoma lines, the presence of the HLA-G2/G4 and G3 isoforms can be observed, which protect these lines against NK-cell-induced cell lysis, as does the HLA-G1 isoform in other lines.

In other lines, all of the HLA-G transcripts are detected. The HLA-G1 protein form is detected by immunofluorescence with an anti-HLA-G antibody, and inhibits NK lysis.

The analysis of biopsies from patients with melanomas reveals a high level of HLA-G transcripts in some tumours (primary and metastases), associated with a high expression of the HLA-G1 protein which is, detectable by immunohistochemistry on frozen sections using an anti-HLA-G1 antibody.

This high HLA-G transcription and expression is specific for tumour tissue and is not detected in healthy tissue.

In certain melanomas, a dissociation of the transcription of the soluble (G5) and membrane-bound isoforms is observed. The analysis of patients reveals 4 HLA-G transcription and expression profiles.

| Transcription profiles | Membrane-bound forms HLA-G1, G2, G3, G4 | Soluble forms |
|---|---|---|
| Profile | | |
| 1 | − | − |
| 2 | ++ | − |
| 3 | − | ++ |
| 4 | ++ | ++ |

The expression of the soluble protein is detected by immunohistochemistry on patients exhibiting profile P4.

A subject of the present invention is also a method for establishing the HLA-G expression profile of a solid tumour with a view to selecting a treatment which is suited to said tumour and/or with a view to monitoring the evolution of said tumour, characterized in that it comprises:

(i) the removal of a tumour sample, (ii) the preparation of a histological section from said sample, (iii) the labelling of the cells of the sample obtained in (ii) with antibodies specific for HLA-G membrane-bound and soluble isoforms, and (iv) the establishment of the HLA-G expression profile of said sample by detecting the labelled cells.

A subject of the present invention is also a method for establishing the HLA-G expression profile of a solid tumour with a view to selecting a treatment which is suited to said tumour and/or with a view to monitoring the evolution of said tumour, characterized in that it comprises:

(i) the removal of a tumour sample, (ii) optionally, the labelling of the cells of said sample, (iii) the lysis of the cells, (iv) the bringing of the lysed cells into contact with various antibodies directed against the class I HLA antigens so as to possibly form HLA-G isoform/antibody complexes, and (v) the establishment of the HLA-G expression profile of said sample by detecting the complexes formed in step (iv).

Preferably, in step (iv), immunoprecipitates are obtained which are separated in step (v) by electrophoresis, transferred onto membrane and detected.

In accordance with the invention, said antibodies are preferably monoclonal antibodies.

The investigation of an HLA-G expression by certain tumour cells and/or cells infiltrating the tumour (macrophages, dendritic cells) makes it possible to better evaluate the potentially effective type of treatment.

Specifically, knowledge of the HLA-G expression transcription profile of a solid tumour is vital for choosing the best possible treatment and for following the evolution of the tumour as a function of said treatment.

A subject of the present invention is also a method for selecting factors for regulating the transcription and/or the expression of HLA-Gs by tumour cells (inhibition), this method being characterized in that it comprises:

(i) the removal of a tumour sample, (ii) the isolation of the tumour cells from said sample, (iii) the primary culture of the tumour cells obtained in (ii), (iv) the addition of the substance to be tested, (v) the visualization of the effect obtained by establishing the HLA-G transcription and/or expression profile of said tumour cells after treatment with said substance to be tested, and (vi) the testing in vitro of the effect of the treatment on the antitumour response (NK and CTL responses).

Advantageously, the cell lines derived from the biopsies make it possible to evaluate the sensitivity to a treatment in vitro, and to determine the agents which are capable of reducing the HLA-G expression (the screening tool) with the aim of re-establishing a better antitumour response, in the case of HLA-G-positive tumour cells.

Such cells are advantageously used as a model for studying the transcription and/or the expression of HLA-Gs.

A subject of the present invention is also a method for monitoring the evolution of a tumour expressing HLA-G, characterized in that it comprises assaying the soluble form of HLA-G in the sera of patients, as a prognostic factor for tumour dissemination or for the capacity of the tumour to form metastases.

Said assaying is preferably carried out by a conventional immunological method, using anti-soluble HLA-G antibodies.

A subject of the present invention is also an antitumour vaccine which can be used for solid tumours expressing at least one HLA-G isoform, characterized in that it is selected from the group consisting of autologous tumour cells and a soluble HLA-G5 antigen or a fragment thereof; such vaccines induce the formation of tumour-specific cytotoxic T lymphocytes and of anti-HLA-G antibodies.

When said vaccine consists of autologous cells (in particular tumour cells from the individual to be treated which express at least one HLA-G isoform), said cells are preferably modified so as to effectively induce, the production of anti-HLA-G antibodies. The cells are, for example, subjected to a cholesterol treatment or to a hyperbaric treatment.

Advantageously, said soluble HLA-G antigen, or a fragment thereof, is coupled to a suitable protein and optionally combined with an adjuvant such as aluminium hydroxide or calcium phosphate.

Said vaccine is preferably administered subcutaneously or intradermally.

A subject of the present invention is also an antitumour composition which can be used for solid tumours expressing at least one HLA-G isoform, characterized in that it consists essentially of anti-HLA-G antibodies (passive immunotherapy).

A subject of the present invention is also an antitumour composition which can be, used for solid tumours expressing at least one HLA-G isoform, characterized in that it consists essentially, of at least one factor for regulating the transcription and/or the expression of HLA-Gs.

According to one advantageous embodiment of said composition, said regulation factor is selected from the group consisting of the regulation factors obtained using the method as defined above, factors which are antagonists of HLA-G activation agents, which have been identified by the inventors [interleukin-10, glucocorticoid, interferons, stress action (radiation, heat shock, heavy metals, oxidative stress)], antisense nucleic acids and hormonal inhibitors of the transcription and/or of the expression of said HLA-Gs.

A subject of the present invention is also products containing anti-HLA-G antibodies and factors for regulating the expression of HLA-Gs as combination products for simultaneous or separate use, or use which is spread out over time, in the treatment of solid tumours expressing at least one HLA-G isoform.

Said regulation factors are as those defined above.

Besides the preceding arrangements, the invention also comprises other arrangements which will emerge from the description which follows, which refers to examples of implementation of the present invention, as well as to the attached drawings in which:

It should be fully understood, however, that these examples are given only by way of illustration of the subject of the invention, of which they in no way constitute a limitation.

EXAMPLE 1

Analysis of the HLA-G Profiles of Various Tumour Lines and Study of the Inhibition of Lysis by NK Cells

A/MATERIALS AND METHODS

1/Cell Lines

The K562 human erythroleukaemia cell line (ATCC) and the immature T cell leukaemia line (clone YT2C2-PR) with NK activity are maintained in an RPMI 1640 medium supplemented with heat-inactivated foetal calf serum at 10%, 2mM L-glutamine, 1 $\mu$g/ml of gentamicin and fungizone (Sigma, Saint-Quentin, France), and cultured at 37° C. in a humidified incubator in an atmosphere which is enriched with 5% $CO_2$. The K562 transfectants are selected in a medium containing 1 mg/ml of geneticin (G418 sulphate, Sigma).

The HLA-G-positive human choriocarcinoma cell line, named JEG-3 (ATCC), is cultured in a DMEM medium (Sigma) supplemented with heat-inactivated foetal calf serum at 10% antibiotics and 2 mM L-glutamine. The cell lines do not contain mycoplasmas.

Besides the abovementioned lines, use is made of:

IGR (HLA-A2, A3, B58/male), M74 (HLA-A1, A2, B8, B14/female), M8 (HLA-A1, A2, B12 and B40/male) and DRAN (HLA-A2, A3, B7, B35, CW5, CW7) melanoma lines, first trimester trophoblastic tissues, which are obtained after abortion; these tissues are cut up into thin slices and immediately used to extract the RNA, and peripheral blood mononucleated cells (PBMC), which are obtained from healthy volunteers and isolated on a Ficoll-Hypaque 1077 density gradient.

2/Monoclonal Antibodies

The following antibodies are used:

W6/32: anti-B$\beta$2-m-associated class I HLA $\alpha$ chain IgG2a (Sigma); HCA2: anti-HLA-A and G IgG and anti-HLA-G IgG, 87G, 4H84 and 16G1.

3/RT-PCR

Total RNA is extracted from $10^7$ cells using the NOW RNA reagent (Biogentex, Inc.) in accordance with the manufacturer's recommendations. The quantity of the RNA is verified by electrophoresis on denaturing 1.5% agarose gel. The cDNAs are prepared from 10 $\mu$g of total RNA treated with DNAse I (Boehringer Mannheim) using an oligo-(dT)$_{12-18}$ primer and the M-MLV reverse transcriptase (GIBCO-BRL). The HLA-G-specific RT-PCR amplifications are carried out using the following primers: G.257 (exon 2) and G3.U (3'UT) (Ishitani A. et al., Proc. Natl. Acad. Sci., 1992, 89, 3947–3951; Kirszenbaum M. et al., Proc. Natl. Acad. Sci., 1994, 91, 4209–4213 and Moreau P. et al., C.R. Acad. Sci., 1995, 318, 837–842) so as to detect all the HLA-G mRNA isoforms. An amplification specific for each HLA-G mRNA form is carried out using the following sets of primers:

G.526 (exon 3) and G3.U (3' UT) for the isoforms G1, G4 and G5;

G.526 (exon 3) and G.i4b (intron 4) for the isoform G5;

G.-3 (partially covering exons 2 and 4) and G3.U (3'UT) for the isoforms G2 and G6;

G.3–4 (partially covering exons 2 and 5) and G3.U (3' UT)for the isoform G3.

The cDNAs of the conventional class I HLAs are amplified as described in King et al. (J. Immunol., 1996, 156, 2068–2076), using a unique 5' primer, HLA-5P2, and 3 3' primers, HLA-3pA, HLA-3pB and HLA-3pC, which amplify the mRNAs HLA-A, HLA-B and HLA-C, respectively.

The DRA specific primers are described in King et al., mentioned above.

A coamplification of the $\beta$-actin cDNA is carried out in each experiment using the Clontech test (16 cycles), so as to evaluate the comparative amounts of RNA in the samples.

The PCR products are analysed by electrophoresis on 1% agarose gel and stained with ethidium bromide. The specificity of the PCR products is confirmed by alkaline blotting of the fragments in 0.4 N NaOH on nylon membranes (Hybond N+, Amersham, France).

The specific HLA-G probes are as follows:

GR, specific for exon 2,

G.647 F (5'-CCACCACCCTGTCTTTGACT (SEQ ID NO: 17): specific for exon 4),

G.I4 F (GAGGCATCATGTCTGTTAGG (SEQ ID NO: 18): specific for intron 4), and

G.927 F (5'-ATCATGGGTATCGTTGCTGG (SEQ ID NO: 19): specific for exon 5).

The other probes are as follows:

HLA-A-specific probe (5'GGAGGACCAGACCCAGGACACG) SEQ ID NO:20),

HLA-B-specific probe (5'AGCTCCGATGACCACAACTGC) (SEQ ID NO:21)

HLA-C-specific probe (5'TGTCCTAGCTGCCTAGGAG) (SEQ ID NO:22) and

HLA-DRA-specific probe (TGTGATCATCCAGGCCGAG) (SEQ ID NO:23).

The filters are exposed onto Kodak films (Biomax) with amplifying screens for 4 to 16 hours at −80° C.

4/Immunoprecipitation of the Surface Biotinylated Proteins and Western Blot.

The surface proteins are labelled with biotin. After washing in PBS, $1.5 \times 10^7$ cells are incubated in 1 ml of cold PBS containing 5 ml of NHS-SS-biotin (Pierce, Rockford, Ill.) for 15 min at 4° C. The residual active groups are inhibited in 50 mM $NH_4Cl$ for 10 min at 4° C. The cells are lysed in 1% Triton X100/PBS. The proteins which are precipitated with the W6/32 antibody are separated on 12% SDS-PAGE, transferred onto nitrocellulose membrane and placed together with a horseradish peroxidase-streptavidin conjugant. After thorough washing of the membrane, the staining reaction is carried out using the ECL Western blotting detection reagent (Amersham, France), after which the membrane is exposed to a Kodak film at room temperature.

5/Cytotoxicity Assays

The cytolytic activity of peripheral blood mononucleated cells, of NK cells and of YT2C2-PR cells (effector cells or E) towards the HLA-G transfectants (target cells or T) is estimated with the aid of chromium 51 4-hour release assays in which the effector cells are mixed with $5 \times 10^3$ target cells which are labelled with chromium 51 (100 µCi of sodium $^{51}$Cr-chromate Amersham, UK), at various E/T ratios, in microtitration plates which have a U-shaped bottom.

After 4 hours at 37° C. in a humidified incubator containing 5% $CO_2$, 100 µl of supernatant are removed for liquid phase scintillation counting (Wallac 1450 Microbeta, Pharmacia, France). The percentage of specific lysis is calculated as follows: percentage of specific lysis=[(cpm in the experimental well−cpm of spontaneous release)/(cpm of maximum release−cpm of spontaneous release)]×100.

The spontaneous release is determined by incubating the labelled target cells (T) with the medium. The maximum release is determined by solubilizing the target cells in 0.1 M HCl. In all the experiments, the spontaneous release is less than 10% with respect to the maximum release. The results are presented as the means of three samples. In the experiments in which the monoclonal antibodies are used to block HLA-G-NK interaction, the target cells are incubated with the corresponding monoclonal antibody, and then washed and incubated with a goat anti-mouse $F(ab')_2$ antibody (Jackson Immunoresearch, USA) in order to avoid antibody-dependent cell cytotoxicity (ADCC) by interaction of the receptors for the immunoglobulin Fc fragment, which are expressed on NK cells, with the primary antibody used. The monoclonal antibody toxicities are also verified in each assay and are always less than 3%.

II-Results

1/Identification of the Various HLA-G Transcripts in Melanoma Cell Lines.

The HLA-G cDNAs of 4 melanoma cell lines (IGR, M8, M74 and DRAN) are amplified with the aid of the previously described primers (A. Ishitani et al., *Proc. Natl. Acad. Sci. USA*, 1992, 89, 3947–3951; M. Kirszenbaum et al., *Proc. Natl. Acad. Sci. USA*, 1994, 91, 4209–4213), which are derived from the sequences which are specific for exon 2 and for the untranslated 3' region (see Materials and Methods) (FIG. 1).

The JEG-3 choriocarcinoma line and trophoblastic cells, which exhibit high levels of HLA-G transcripts, are used as positive controls and the peripheral blood mononucleated cells (PBMC) of healthy volunteers are used as negative controls (low levels of HLA-G transcripts).

The hybridization of the PCR products made it possible to identify significant levels of HLA-G mRNA in 2 melanoma cell lines, namely IGR and M74; whereas no signal can be detected in the M8 melanoma cell line.

Figure 1A:
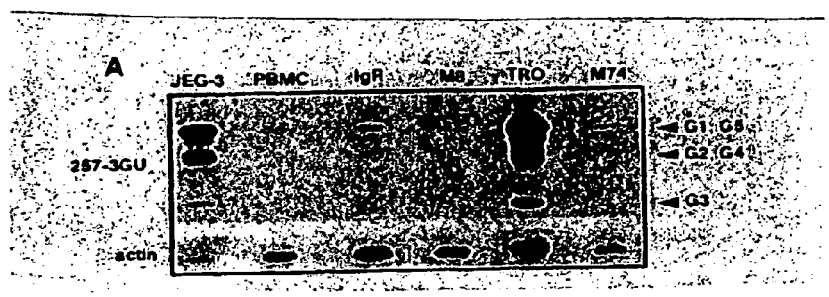
FIG. 1 illustrates.
Figure 1B:
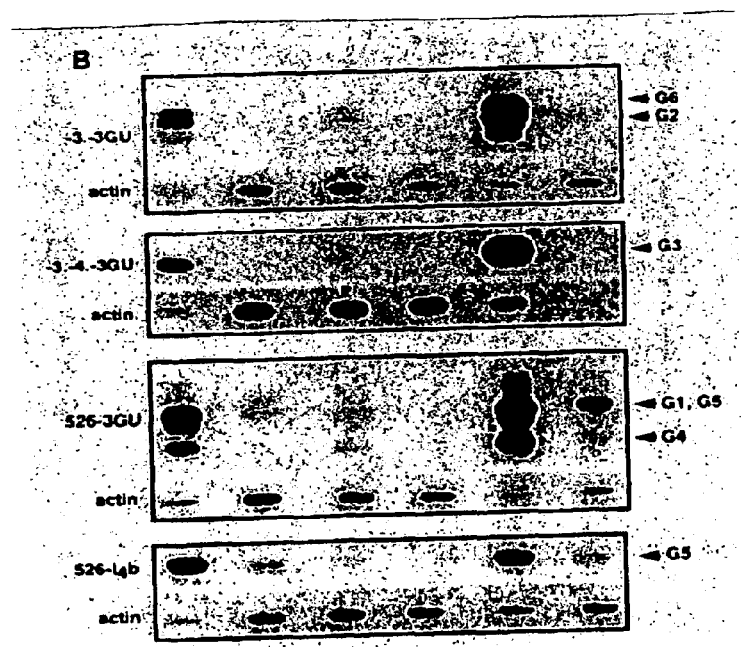
Figure 1C:
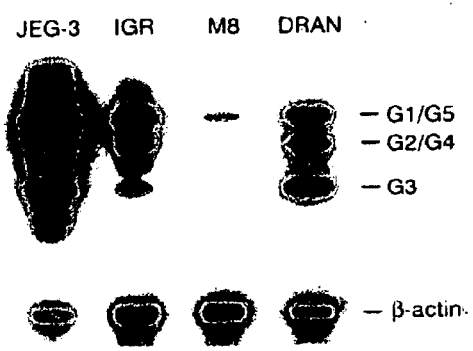

In the JEG-3 cells and trophoblasts, all the HLA-G transcripts are detected (FIGS. 1A and 1C).

In the IGR and DRAN melanoma cells, all the transcripts are also detected by the pan-HLA-G primers (FIGS. 1A and 1C).

However, the pan-HLA-G primers do not make it possible to distinguish between the HLA-G1 and HLA-G5 signals, which are both present, in a band corresponding to 1000 bp, nor between the HLA-G2 and HLA-G1 signals, which comigrate in the form of a 600-bp fragment. RT-PCR identification makes it possible to isolate the isoforms with the aid of specific primers (P. Moreau et al., *C.R. Acad. Sci.*, 1995, 318, 837–842) (see Materials and Methods).

The IGR and DRAN cells express all the HLA-G isoforms in the form of transcripts, HLA-G4 and HLA-G5 being expressed at low levels (FIG. 1B).

In the M74 melanoma cell line, the pan-HLA-G primers detect bands corresponding to HLA-G1 and HLA-G5 (1000 bp) (strong signals), a signal for HLA-G2 and G4 (600 bp), but no signal for HLA-G3 (300 bp) (FIG. 1A). The primers for the specific isoforms reveal that, in these cells, the G1 and G4 isoforms are more abundant than in the PBMCs, while the level of G5 transcript is comparable to that observed in the PBMCs.

Low levels of HLA-G2 and HLA-G6 (soluble form of HLA-G2) mRNA are detected in these M74 cells, while specific amplification of the HLA-G3 transcript confirms the absence of HLA-G3 which is observed with the pan-HLA-G primers in these cells (FIGS. 1A and 1B).

No HLA-G hybridization signal is observed in M8 cells (FIGS. 1A and 1B).

2/Analysis of the HLA-G Proteins in Melanoma Cells.

In order to determine whether the HLA-G transcripts which are detected in the melanomas are translated into HLA-G proteins, immunoprecipitation studies were carried out with various anti-HLA class I monoclonal antibodies.

The comparison is performed in the presence of a positive control (JEG-3 cell) and a negative control (M8 melanoma cells).

The results of immunoprecipitation with the W6/32 monoclonal antibody are illustrated in FIG. 3.

With the JEG-3 cells, the W6/32 antibody immunoprecipitated two proteins of 45 KDa (HLA-C molecule) and of 39 KDa (membrane bound HLA-G1 isoform).

In the IGR and M8 cells, only one protein of 45 KDa is detected.

Similar results are obtained by immunoprecipitation of biotinylated surface proteins (FIG. 3).

These data show that the HLA-G1 protein is not expressed in the IGR cells, even though the latter express the corresponding mRNA.

However, the absence of HLA-G1 protein in the IGR cells does not exclude the expression of 3 other HLA-G isoforms (HLA-G2, G3 and G4).

These proteins cannot be revealed by the W6/32 monoclonal antibody, because of their inability to associate with β2m.

To reveal these proteins, immunoprecipitation of methionine-labelled ($^{35}$S-methionine) proteins is carried out using monoclonal antibodies which recognize. free HLA-G, denatured HLA-G and HLA-A (HCA2 antibodies) and an epitope which is located in the α1 domain which is present in all the isoforms of the HLA-G protein (anti-HLA-G Ig monoclonal antibody).

The monoclonal antibody reveals the presence of the 39-KDa HLA-G1 protein in the JEG-3 and DRAN cells, and its absence in the IGR cells (FIG. 4).

Additional bands, which migrate at 32 to 34 KDa and at 18 KDa, and which correspond to the size of the HLA-G2 protein and/or of the HLA-G4 or G3 protein, respectively, are detected in the IGR cells both with the anti-HLA-G Ig monoclonal antibody and with the HCA2 antibody (FIG. 4).

The additional bands, which are specific to the HLA-G protein, are not observed in the M74 and M8 cells, which do not exhibit the corresponding HLA-G transcripts (FIG. 4).

3/Protection of the IGR Line Against NK Cell-induced Cytolysis.

The YT2C2-PR cells are used as NK effector cells.

The IGR cell line, which expresses the HLA-G2 and/or G4 and G3 isoforms, and the DRAN line, which expresses HLA-G1, abolish clone YT2C2-PR-induced lysis (FIG. 5).

The M74 melanoma cell line, which expresses the conventional MHC class I antigens, but which exhibits a selective deficiency in the transcription and expression of the HLA-G2 and HLA-G3 isoforms, is lysed by the clone YT2CT-PR.

Lysis is also observed with the M8 cell line, which expresses the conventional MHC class I antigens, but which transcribes no HLA-G mRNA (FIGS. 1 and 5).

In order to show that only the HLA-Gs are involved in this inhibition of NK cell-induced lysis, several EBV-B cell lines which express no HLA-G, but which share at least one HLA-A, B or C allele with the IGR line, are used as target cells.

All these EBV-B lines are lysed by the clone YT2C2-PR, showing that the HLA-A, B and C antigens are not involved in protecting the IGR and DRAN melanomas against the YT2C2-PR lysis (FIG. 5).

In order to show that the clone YT2C2-PR-induced lysis, by the IGR cells, is not due to a signal which is transmitted by this cell line, but is indeed linked to an intrinsic resistance of these IGR cells to NK cells, the IGR cells were used as inhibitors in a cytotoxicity assay in which the target cells (T) are M8 cells and the YT2C2-PR cells are the effector cells (E).

FIG. 5B shows that the IGR cells effectively inhibit lysis of the M8 cells by the clone YT2C2-PR; this inhibition is proportional to the number of IGR cells used for the competitive assay).

EXAMPLE 2

Detection of HLA-G Transcripts and Proteins in Melanoma Biopsies

A/MATERIALS AND METHODS

1/Tumour Samples

Biopsies are performed on tissue samples from patients.

Immediately after removal, the samples are frozen in liquid nitrogen and stored until extraction of the RNA.

2/Immunohistochemistry

Standard methods are used to carry out the immunohistochemistry on sections which are prepared from the melanoma biopsies, fixed with acetone, rinsed in PBS and blocked in normal rabbit serum (DAKO) in PBS.

The samples are incubated with the primary antibody for 1 h at room temperature, and are then incubated with a secondary antibody (FITC-conjugated rabbit anti-mouse Ig) (DAKO).

The sections are counterstained with a nuclear dye (DAPI, Sigma) and prepared in a suitable medium. The fluorescence is analysed using an Io24 MRC confocal microscope (Bio-Rad). The following antibodies are used: W6/32: anti-β2-microglobulin-associated HLA-G class I heavy chain IgG2a (Sigma) and 87G: anti-HLA-G IgG2b which detects the HLA-G1 isoform.

The other techniques are identical to those in Example 1.

B/RESULTS

1/Analysis of HLA-G Transcription in Melanoma Biopsies Ex Vivo.

In some melanoma biopsies, all the HLA-G transcripts are detected at significant levels, whereas only the 1000-bp band is detected in the healthy human skin (FIGS. 2 and 6). These results were confirmed on other biopsies and show that the significant transcription levels observed in the melanoma cells are specific for the latter and cannot be observed in healthy tissue.

More precisely, high levels of HLA-G go transcription are detected specifically in primary tumours and in metastases, whereas basal levels of HLA-G transcripts and an absence of expression of HLA-G protein are observed in healthy skin or in normal lymph nodes (FIG. 6A).

The analysis of the healthy skin (HS1), of the skin primary tumours (SP1) and of a tumour regression site (R1) in a skin primary tumour from the same patient enables the detection of a high level of HLA-G transcripts and of protein expression at the primary tumour site, whereas both the healthy skin and the tumour regression site exhibit basal levels of HLA-G transcripts and a complete absence of the expression of HLA-G1 proteins (FIG. 7).

The cultured primary cells (MPP5) which are derived from the primary tumour SP1 also exhibit high levels of HLA-G transcripts (FIG. 7).

2/Analysis of Soluble HLA-G Transcription in Melanoma Biopsies Ex Vivo

Specific amplification of the transcripts (mRNA) corresponding to the HLA-G5 soluble isoform in the melanoma biopsies shows that high levels of HLA-G5 transcripts are detected in certain melanoma biopsies which have been shown to exhibit high levels of transcripts corresponding to the membrane-bound isoforms of HLA-G (FIG. 8).

Moreover, in other cases, a dissociation is observed between the HLA-G5 levels and the levels of the other HLA-G transcripts: in melanoma biopsies in which high HLA-G1, G2, G3 and G4 levels have previously been observed, HLA-G5 transcripts are not observed.

The skin primary tumour SP1 and the corresponding cultured cells MPP5, as well as the lymph node metastases LNM2, exhibit high, levels of HLA-G transcripts corresponding to membrane-bound HLA-G isoforms (FIG. 8) whereas HLA-G5 transcripts are not detected in the same sample.

3/Analysis of the Membrane-bound and Soluble Proteins in Melanoma Biopsies

High levels of HLA-G transcripts are correlated with the specific detection of the expression of HLA-G protein by an anti-HLA-G monoclonal antibody (antibody 87G) in melanoma biopsies. Specifically, the immunohistochemical analysis of the HLA-G expression in a metastatic lymph node (LNM2) biopsy makes it possible to observe positive staining of LNM2 both with the antibody 87G and with the antibody W6/32, whereas the negative control, which consists of healthy skin from the same patient, is not stained with the anti-HLA-G antibody.

In order to refine this study, an antibody which specifically detects the soluble HLA-G protein, the antibody 16G1 (Lee et al., Immunity, 1995, 3, 591–600), makes it possible to demonstrate the expression of the soluble HLA-G protein in the lymph node biopsy of a patient exhibiting high levels of HLA-G5 transcripts (FIG. 8).

The immunohistochemical analysis enables the staining of this biopsy, while no detectable expression is observed, using the same antibody, in a melanoma biopsy of a patient exhibiting high levels of the other HLA-G isoforms.

Specifically, the immunohistochemical analysis of the expression of soluble HLA-G in the LNM2 biopsy shows that acetone-fixed LNM2 biopsy sections are positively stained with the anti-melanoma antibody HMB45 (DAKO, Glostrup,; Skelton et al., Am. J. Dermatopathol., 1991, 13, 543–550) and the anti-soluble HLA-G antibody 16G1, whereas the negative control is not stained.

As emerges from the above, the invention is in no way limited to the modes of implementation, execution and application which have just been described more explicitly; on the contrary, it encompasses all the variants thereof which may occur to persons skilled in the art, without departing from the context or the scope of the present invention.

What is claimed is:

1. A method for establishing the HLA-G expression profile of a solid tumour with a view to selecting a treatment which is suited to said tumour or with a view to monitoring the evolution of said tumour, comprising:
  i) removing a tumour sample,
  (ii) preparing a histological section from said tumour sample,
  (iii) labeling the uncultured tumour cells of the tumour sample obtained in (ii) with antibodies specific for HLA-G membrane-bound and soluble isoforms, and
  (iv) establishing the HLA-G expression profile of said tumour sample by detecting the labelled tumour cells.

2. A method for establishing the HLA-G expression profile of a solid tumour with a view to selecting treatment which is suited to said tumour or with a view to monitoring the evolution of said tumour, comprising:
  (i) removing a tumour sample,
  (ii) lysing the uncultured tumour cells,
  (iii) contacting the uncultured lysed tumour cells with various antibodies directed against the class I HLA antigens so as to form HLA-G isoform/antibody complexes, and
  (iv) establishing the HLA-G expression profile of said tumour sample by detecting the complexes formed in step (iii).

3. The method of claim 1, wherein the antibodies specific for HLA-G membrane-bound and soluble isoforms are monoclonal antibodies.

4. The method of claim 1, wherein the HLA-G membrane-bound isoforms are HLA-G1, HLA-G2, HLA-G3 and HLA-G4.

5. The method of claim 1, wherein the HLA-G soluble isoforms are HLA-G5 and HLA-G6.

6. The method of claim 2, wherein subsequent to the contacting in (iii) the cells are immunoprecipitated.

7. The method of claim 2, wherein the detecting in (iv) comprises electrophoresis and transfer to a membrane.

8. The method of claim 2, wherein the antibodies specific for HLA-G membrane-bound and soluble isoforms are monoclonal antibodies.

9. The method of claim 2, wherein the HLA-G membrane-bound isoforms are HLA-G1, HLA-G2, HLA-G3 and HLA-G4.

10. The method of claim 2, wherein the HLA-G soluble isoforms are HLA-G5 and HLA-G6.

11. The method of claim 2, wherein the uncultured tumour cells are labeled prior to lysing the tumour cells in (ii).

* * * * *

SEQUENCE LISTING

<160> NUMBER OF SEQ ID NOS: 23

<210> SEQ ID NO 1
<211> LENGTH: 20
<212> TYPE: DNA
<213> ORGANISM: Artificial Sequence
<220> FEATURE:
<223> OTHER INFORMATION: synthetic DNA

<400> SEQUENCE: 1
ggaagaggag acacggaaca                    20

<210> SEQ ID NO 2
<211> LENGTH: 22
<212> TYPE: DNA
<213> ORGANISM: Artificial Sequence
<220> FEATURE:
<223> OTHER INFORMATION: synthetic DNA

<400> SEQUENCE: 2
ggctggtctc tgcacaaaga ga                 22

<210> SEQ ID NO 3
<211> LENGTH: 20
<212> TYPE: DNA
<213> ORGANISM: Artificial Sequence
<220> FEATURE:
<223> OTHER INFORMATION: synthetic DNA

<400> SEQUENCE: 3
ccaatgtggc tgaacaaagg                    20

<210> SEQ ID NO 4
<211> LENGTH: 22
<212> TYPE: DNA
<213> ORGANISM: Artificial Sequence
<220> FEATURE:
<223> OTHER INFORMATION: synthetic DNA

<400> SEQUENCE: 4
ggctggtctc tgcacaaaga ga                 22

```
<210> SEQ ID NO 5
<211> LENGTH: 20
<212> TYPE: DNA
<213> ORGANISM: Artificial Sequence
<220> FEATURE:
<223> OTHER INFORMATION: synthetic DNA

<400> SEQUENCE: 5
accagagcga ggccaagcag                                              20

<210> SEQ ID NO 6
<211> LENGTH: 22
<212> TYPE: DNA
<213> ORGANISM: Artificial Sequence
<220> FEATURE:
<223> OTHER INFORMATION: synthetic DNA

<400> SEQUENCE: 6
ggctggtctc tgcacaaaga ga                                           22

<210> SEQ ID NO 7
<211> LENGTH: 20
<212> TYPE: DNA
<213> ORGANISM: Artificial Sequence
<220> FEATURE:
<223> OTHER INFORMATION: synthetic DNA

<400> SEQUENCE: 7
accagagcga ggccaacccc                                              20

<210> SEQ ID NO 8
<211> LENGTH: 22
<212> TYPE: DNA
<213> ORGANISM: Artificial Sequence
<220> FEATURE:
<223> OTHER INFORMATION: synthetic DNA

<400> SEQUENCE: 8
ggctggtctc tgcacaaaga ga                                           22

<210> SEQ ID NO 9
<211> LENGTH: 20
<212> TYPE: DNA
<213> ORGANISM: Artificial Sequence
<220> FEATURE:
<223> OTHER INFORMATION: synthetic DNA

<400> SEQUENCE: 9
accagagcga ggccaacccc                                              20

<210> SEQ ID NO 10
<211> LENGTH: 20
<212> TYPE: DNA
<213> ORGANISM: Artificial Sequence
<220> FEATURE:
<223> OTHER INFORMATION: synthetic DNA

<400> SEQUENCE: 10
aaaggaggtg aaggtgaggg                                              20

<210> SEQ ID NO 11
<211> LENGTH: 20
<212> TYPE: DNA
<213> ORGANISM: Artificial Sequence
<220> FEATURE:
<223> OTHER INFORMATION: synthetic DNA
```

```
<400> SEQUENCE: 11
ccaatgtggc tgaacaaagg                                               20

<210> SEQ ID NO 12
<211> LENGTH: 20
<212> TYPE: DNA
<213> ORGANISM: Artificial Sequence
<220> FEATURE:
<223> OTHER INFORMATION: synthetic DNA

<400> SEQUENCE: 12
aaaggaggtg aaggtgaggg                                               20

<210> SEQ ID NO 13
<211> LENGTH: 21
<212> TYPE: DNA
<213> ORGANISM: Artificial Sequence
<220> FEATURE:
<223> OTHER INFORMATION: synthetic DNA

<400> SEQUENCE: 13
ggtctgcagg ttcattctgt c                                             21

<210> SEQ ID NO 14
<211> LENGTH: 20
<212> TYPE: DNA
<213> ORGANISM: Artificial Sequence
<220> FEATURE:
<223> OTHER INFORMATION: synthetic DNA

<400> SEQUENCE: 14
ccaccaccct gtctttgact                                               20

<210> SEQ ID NO 15
<211> LENGTH: 20
<212> TYPE: DNA
<213> ORGANISM: Artificial Sequence
<220> FEATURE:
<223> OTHER INFORMATION: synthetic DNA

<400> SEQUENCE: 15
gaggcatcat gtctgttagg                                               20

<210> SEQ ID NO 16
<211> LENGTH: 20
<212> TYPE: DNA
<213> ORGANISM: Artificial Sequence
<220> FEATURE:
<223> OTHER INFORMATION: synthetic DNA

<400> SEQUENCE: 16
atcatgggta tcgttgctgg                                               20

<210> SEQ ID NO 17
<211> LENGTH: 20
<212> TYPE: DNA
<213> ORGANISM: Artificial Sequence
<220> FEATURE:
<223> OTHER INFORMATION: synthetic DNA

<400> SEQUENCE: 17
ccaccaccct gtctttgact                                               20

<210> SEQ ID NO 18
```

-continued

```
<211> LENGTH: 20
<212> TYPE: DNA
<213> ORGANISM: Artificial Sequence
<220> FEATURE:
<223> OTHER INFORMATION: synthetic DNA

<400> SEQUENCE: 18
gaggcatcat gtctgttagg                                            20

<210> SEQ ID NO 19
<211> LENGTH: 20
<212> TYPE: DNA
<213> ORGANISM: Artificial Sequence
<220> FEATURE:
<223> OTHER INFORMATION: synthetic DNA

<400> SEQUENCE: 19
atcatgggta tcgttgctgg                                            20

<210> SEQ ID NO 20
<211> LENGTH: 22
<212> TYPE: DNA
<213> ORGANISM: Artificial Sequence
<220> FEATURE:
<223> OTHER INFORMATION: synthetic DNA

<400> SEQUENCE: 20
ggaggaccag acccaggaca cg                                         22

<210> SEQ ID NO 21
<211> LENGTH: 21
<212> TYPE: DNA
<213> ORGANISM: Artificial Sequence
<220> FEATURE:
<223> OTHER INFORMATION: synthetic DNA

<400> SEQUENCE: 21
agctccgatg accacaactg c                                          21

<210> SEQ ID NO 22
<211> LENGTH: 19
<212> TYPE: DNA
<213> ORGANISM: Artificial Sequence
<220> FEATURE:
<223> OTHER INFORMATION: synthetic DNA

<400> SEQUENCE: 22
tgtcctagct gcctaggag                                             19

<210> SEQ ID NO 23
<211> LENGTH: 19
<212> TYPE: DNA
<213> ORGANISM: Artificial Sequence
<220> FEATURE:
<223> OTHER INFORMATION: synthetic DNA

<400> SEQUENCE: 23
tgtgatcatc caggccgag                                             19
```